United States Patent
Shiraishi et al.

(10) Patent No.: US 9,001,971 B2
(45) Date of Patent: Apr. 7, 2015

(54) X-RAY DIAGNOSTIC APPARATUS AND X-RAY BEAM LIMITING CONTROL METHOD

(71) Applicants: Kunio Shiraishi, Otawara (JP); Masanori Matsumoto, Nasushiobara (JP); Shumpei Oohashi, Otawara (JP)

(72) Inventors: Kunio Shiraishi, Otawara (JP); Masanori Matsumoto, Nasushiobara (JP); Shumpei Oohashi, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 326 days.

(21) Appl. No.: 13/685,960

(22) Filed: Nov. 27, 2012

(65) Prior Publication Data

US 2013/0142304 A1 Jun. 6, 2013

(30) Foreign Application Priority Data

Dec. 2, 2011 (JP) ................................. 2011-264505

(51) Int. Cl.
*G21K 3/00* (2006.01)
*A61B 6/10* (2006.01)
(Continued)

(52) U.S. Cl.
CPC *G21K 1/10* (2013.01); *G01N 23/02* (2013.01); *A61B 6/4035* (2013.01); *A61B 6/544* (2013.01); *A61B 6/481* (2013.01); *A61B 6/583* (2013.01); *A61B 6/588* (2013.01)

(58) Field of Classification Search
CPC .......... A61B 6/488; A61B 6/54; A61B 6/544; A61B 6/545; A61B 6/582

USPC ........................ 378/16, 62, 95, 114–116, 145, 378/156–158, 204, 210; 359/227, 233, 234, 359/601, 614, 885, 891, 892, 896
See application file for complete search history.

(56) References Cited

U.S. PATENT DOCUMENTS 3,854,049 A * 12/1974 Mistretta et al. ................. 378/62
4,101,766 A * 7/1978 Minami et al. ................. 378/158
(Continued)

FOREIGN PATENT DOCUMENTS

CN 1315434 C 5/2007
JP 10-201750 8/1998
(Continued)

OTHER PUBLICATIONS

"DoseWise, Perfect image. Perfect sense.", Inside Philips Cardio/Vascular X-Ray, Philips, Sep. 2004, 15 pages.
(Continued)

*Primary Examiner* — Jack Berman
*Assistant Examiner* — Eliza Osenbaugh-Stewart
(74) *Attorney, Agent, or Firm* — Oblon, McClelland, Maier & Neustadt, L.L.P.

(57) ABSTRACT

According to one embodiment, an X-ray diagnostic apparatus includes an X-ray generation unit, X-ray detection unit, X-ray beam limiting unit, and X-ray beam limiting control unit. The X-ray generation unit generates X-rays. The X-ray detection unit detects the X-rays generated by the X-ray generation unit and transmitted through an object placed on a tabletop. The X-ray beam limiting unit includes a plurality of filters to harden radiation quality of the generated X-rays. The X-ray beam limiting control unit controls the X-ray beam limiting unit to place a filter between the X-ray generation unit and the object, which filter is specified from the plurality of filters based on the thickness of the object and the distance between the X-ray generation unit and the X-ray detection unit.

11 Claims, 7 Drawing Sheets

(51) Int. Cl.
*G21K 1/10* (2006.01)
*G01N 23/02* (2006.01)
*A61B 6/00* (2006.01)

(56) References Cited

U.S. PATENT DOCUMENTS

| | | | | |
|---|---|---|---|---|
| 4,246,488 | A * | 1/1981 | Hura | 378/151 |
| 2001/0012330 | A1* | 8/2001 | Ogura et al. | 378/95 |
| 2002/0085672 | A1* | 7/2002 | Ganin et al. | 378/108 |
| 2007/0217573 | A1* | 9/2007 | Bernhardt | 378/98.12 |
| 2008/0123816 | A1* | 5/2008 | Mori et al. | 378/156 |

FOREIGN PATENT DOCUMENTS

| | | |
|---|---|---|
| JP | 2003-230556 | 8/2003 |
| JP | 2004-8490 | 1/2004 |
| JP | 2007-97665 | 4/2007 |

OTHER PUBLICATIONS

"Functionality and Operation of Fluoroscopic Automatic Brightness Control/Automatic Dose Rate Control Logic in Modern Cardiovascular and Interventional Angiography Systems", AAPM Report No. 125, A Report of AAPM Task Group 125 Radiography/Fluoroscopy Subcommittee, Imaging Physics Committee, Science Council, Jun. 2012, 51 pages.

Combined Office Action and Search Report issued Jun. 19, 2014 in Chinese Patent Application No. 201210495252.7 (with English translation).

* cited by examiner

| X-ray condition (maximum power) (power: kW) | Entrance dose rate (upper limit value) on object (mGy/min) | SID(cm) | Object thickness (THK) THK≦12cm | Object thickness (THK) 12cm<THK≦15cm | Object thickness (THK) 15cm<THK≦22cm | Object thickness (THK) 22cm<THK |
|---|---|---|---|---|---|---|
| 3.0 | 50 | SID≦105 | First additional filter | First additional filter | First additional filter | Second additional filter |
| | | 105<SID≦115 | | | Second additional filter | Fourth additional filter |
| | | 115<SID | | | | |
| | 125 | SID≦105 | Second additional filter | Fourth additional filter | Fourth additional filter | Third additional filter |
| | | 105<SID≦115 | | | Fifth additional filter | Fifth additional filter |
| | | 115<SID | | | | |
| | 87 | SID≦102 | First additional filter | First additional filter | First additional filter | Second additional filter |
| | | 102<SID≦115 | | | Second additional filter | Fourth additional filter |
| | | 115<SID | | | | Fifth additional filter | a

| X-ray condition (maximum power) (power: kW) | Entrance dose rate (upper limit value) on object (mGy/min) | SID(cm) | Object thickness (THK) THK≦12cm | Object thickness (THK) 12cm<THK≦15cm | Object thickness (THK) 15cm<THK≦22cm | Object thickness (THK) 22cm<THK |
|---|---|---|---|---|---|---|
| 2.2 | 50 | SID≦105 | Third additional filter | Third additional filter | Third additional filter | Fourth additional filter |
| | | 105<SID≦115 | | | Fourth additional filter | Sixth additional filter |
| | | 115<SID | | | | |
| | 125 | SID≦105 | Fourth additional filter | Sixth additional filter | Sixth additional filter | Fifth additional filter |
| | | 105<SID≦115 | | | Seventh additional filter | Seventh additional filter |
| | | 115<SID | | | | |
| | 87 | SID≦102 | Third additional filter | Third additional filter | Third additional filter | Fourth additional filter |
| | | 102<SID≦115 | | | Fifth additional filter | Sixth additional filter |
| | | 115<SID | | | | Seventh additional filter | b

X-RAY DIAGNOSTIC APPARATUS AND X-RAY BEAM LIMITING CONTROL METHOD

CROSS-REFERENCE TO RELATED APPLICATIONS

This application is based upon and claims the benefit of priority from Japanese Patent Application No. 2011-264505, filed Dec. 2, 2011, the entire contents of which are incorporated herein by reference.

FIELD

Embodiments described herein relate generally to an X-ray diagnostic apparatus and an X-ray beam limiting control method.

BACKGROUND

Conventionally, an X-ray diagnostic apparatus includes an X-ray beam limiting unit which can adjust an X-ray irradiation field. The X-ray beam limiting unit includes a plurality of filters (to be referred to as additional filters hereinafter) having different thicknesses to adjust the radiation quality of X-rays. Such an additional filter (also called a radiation quality filter or beam spectrum filter) can reduce soft X-rays generated by an X-ray generation unit in an X-ray diagnostic apparatus. The apparatus executes switching of a plurality of additional filters based on the object thickness estimated from conditions for the generation of X-rays (to be referred to as X-ray conditions hereinafter) and the like or the SID (Source Image Distance).

When switching (to be referred to as an object thickness switching method hereinafter) additional filters based on an estimated object thickness, the following problem arises. If the object thickness is small, the apparatus uses an additional filter exhibiting a high elimination efficiency of soft X-rays (X-rays having relatively long wavelengths and low penetrating powers) (in general, a thick additional filter). In contrast, if the estimated object thickness is large, since X-ray conditions (e.g., the maximum output of an X-ray tube and a restriction on the entrance X-ray dose on an object) tend to reach their upper limits at the time of fluoroscopy or the like, the apparatus uses an additional filter exhibiting a high X-ray transmittance (an additional filter exhibiting a low elimination efficiency of soft X-rays: a thin additional filter in general). If the object thickness is large, the X-ray diagnostic apparatus uses a thin additional filter in spite of the fact that it has a capacity enough to generate X-rays having high penetrating power. This leads to a problem that the maximum thickness of a filter which can be used for imaging or fluoroscopy becomes smaller than that of a filter which can be used for imaging or fluoroscopy by using the above capacity to the full.

A method of avoiding the above problem is a method of switching additional filters in accordance with the magnitude of SID (to be referred to as an SID-dependent switching method hereinafter). This method allows to ensure the maximum thickness of a filter which can be used for imaging and fluoroscopy by making an X-ray diagnostic apparatus use the capacity of generating X-rays having high penetrating power. However, the SID-dependent switching method uses a thin additional filter regardless of the object thickness if the SID is long, and hence the exposure dose becomes higher than that in the object-thickness-dependent switching method. In addition, the object-thickness-dependent switching method and the SID-dependent switching method have the problem of a deterioration in image quality.

BRIEF DESCRIPTION OF THE DRAWINGS

FIG. 5 is a view showing an example of a correspondence table of additional filters corresponding to an X-ray condition, entrance X-ray dose rates (upper limit values) on objects, SIDs, and object thicknesses according to the first modification of the first embodiment.

DETAILED DESCRIPTION

In general, according to one embodiment, an X-ray diagnostic apparatus includes an X-ray generation unit, an X-ray detection unit, an X-ray beam limiting unit, and an X-ray beam limiting control unit. The X-ray generation unit is configured to generate X-rays. The X-ray detection unit is configured to detect the X-rays generated by the X-ray generation unit and transmitted through an object placed on a tabletop. The X-ray beam limiting unit includes a plurality of filters configured to harden radiation quality of the generated X-rays. The X-ray beam limiting control unit is configured to control the X-ray beam limiting unit to place a filter of the plurality of filters between the X-ray generation unit and the object, said filter of the plurality of filters being specified based on a thickness of the object and a distance between the X-ray generation unit and the X-ray detection unit.

An X-ray diagnostic apparatus according to an embodiment will be described below with reference to the accompanying drawing. Note that the same reference numerals in the following description denote constituent elements having almost the same functions and arrangements, and a repetitive description will be made only when required.

(First Embodiment)

Figure 1:
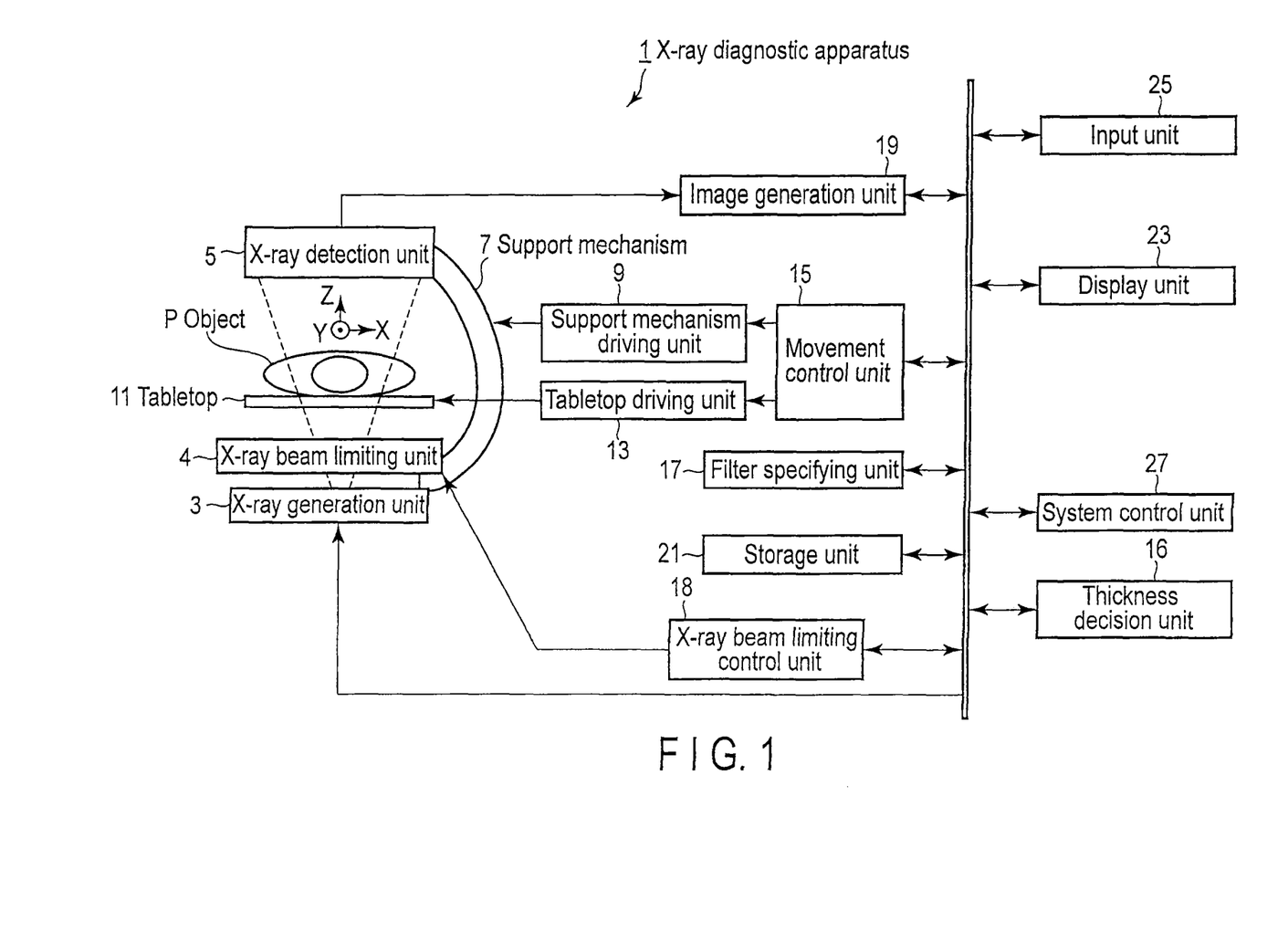
FIG. 1 is a block diagram showing an example of the arrangement of an X-ray diagnostic apparatus according to the first embodiment.

FIG. 1 shows the arrangement of an X-ray diagnostic apparatus 1 according to this embodiment. The X-ray diagnostic apparatus 1 includes an X-ray generation unit 3, an X-ray beam limiting unit 4, an X-ray detection unit 5, a support mechanism 7, a support mechanism driving unit 9, a tabletop 11, a tabletop driving unit 13, a movement control unit 15, a thickness decision unit 16, a filter specifying unit 17, an X-ray beam limiting control unit 18, an image generation unit 19, a storage unit 21, a display unit 23, an input unit 25, and a system control unit 27.

The X-ray generation unit 3 includes an X-ray tube and a high voltage generation unit (neither of which is shown). The high voltage generation unit generates a tube current to be supplied to the X-ray tube and a high voltage to be applied to the X-ray tube. The high voltage generation unit supplies tube currents suitable for X-ray imaging and X-ray fluoroscopy, respectively, to the X-ray tube. The high voltage generation unit applies tube voltages suitable for X-ray imaging and X-ray fluoroscopy, respectively, to the X-ray tube. The X-ray tube generates X-rays with an X-ray focus (to be referred to as a tube focus hereinafter) based on the tube current supplied from the high voltage generation unit and the tube voltage applied from the high voltage generation unit.

The X-ray beam limiting unit 4 is provided between the X-ray generation unit and the object placed on the tabletop 11 (to be described later). More specifically, the X-ray beam limiting unit 4 is provided at the X-ray irradiation window of the X-ray generation unit 3. The X-ray beam limiting unit 4 focuses the X-rays generated by the X-ray generation unit 3 to the size of a predetermined irradiation field to prevent regions other than an observation region from being unnecessarily exposed to X-rays. The X-ray beam limiting unit 4 includes a plurality of filters (to be referred to as additional filters hereinafter) to be inserted in a cone of X-rays to be used in order to reduce the exposure dose of the object and improve image quality. Each of the plurality of additional filters is a plate member formed from a thin metal plate (e.g., an aluminum, copper, molybdenum, or tantalum plate). The plurality of additional filters respectively have different thicknesses. An additional filter is also called an X-ray filter, filtration plate, beam filter, radiation quality filter, or beam spectrum filter. The X-ray beam limiting unit 4 places at least one of the plurality of additional filters in front of the X-ray irradiation window under the control of the X-ray beam limiting control unit 18.

Each of the plurality of additional filters removes long-wavelength components of the continuous spectrum X-rays generated by the X-ray generation unit 3 in accordance with the thickness of the additional filter. Each of the plurality of additional filters hardens the radiation quality of the X-rays generated by the X-ray generation unit 3 by removing long-wavelength components in accordance with the thickness. In addition, each of the plurality of additional filters can remove X-ray energy components unnecessary for X-ray diagnosis. This makes it possible to use each of the plurality of additional filters for the adjustment of the radiation quality of the X-rays generated by the X-ray generation unit 3. The X-ray beam limiting unit 4 places the additional filter specified by the filter specifying unit 17 (to be described later) in front of the X-ray irradiation window of the X-ray generation unit 3 under the control of the X-ray beam limiting control unit 18 (to be described later).

The X-ray detection unit 5 detects the X-rays generated from the X-ray generation unit 3 and transmitted through an object P. The X-ray detection unit 5 includes an FPD (Flat Panel Detector). The FPD includes a plurality of semiconductor detection elements. Semiconductor detection elements are classified into a direct conversion type and an indirect conversion type. The direct conversion type is a scheme of directly converting incident X-rays into an electrical signal. The indirect conversion type is a scheme of converting incident X-rays into light via a phosphor and converting the light into an electrical signal. The electrical signals generated by a plurality of semiconductor detection elements upon incidence of X-rays are output to an A/D converter (Analog to Digital converter) (not shown). The A/D converter converts an electrical signal into digital data. The A/D converter outputs the digital data to a preprocessing unit (not shown). Note that the X-ray detection unit 5 may use an image intensifier or the like.

The preprocessing unit (not shown) executes preprocessing for the digital data output from the X-ray detection unit 5. The preprocessing includes correction of sensitivity unevenness among the channels in the X-ray detection unit 5 and correction concerning an extreme deterioration in signals or omission of data due to a strong X-ray absorber such as a metal. The preprocessed digital data is output to the image generation unit 19 (to be described later).

The support mechanism 7 movably supports the X-ray generation unit 3 and the X-ray detection unit 5. More specifically, the support mechanism 7 includes, for example, a C-arm and a C-arm support portion (neither of which is shown). The C-arm supports the X-ray generation unit 3 and the X-ray detection unit 5 so as to make them face each other. Note that an Ω-arm may be used in place of the C-arm. In addition, the C-arm supports the X-ray generation unit 3 and the X-ray detection unit 5 so as to be able to change the distance (SID (Source Image Distance)) between the X-ray generation unit 3 and the X-ray detection unit 5. The C-arm support portion supports the C-arm so as to make it slidable in a direction along the C shape of the arm (to be referred to as the first direction hereinafter). The C-arm support portion supports the C-arm so as to allow the C-arm to pivot about the connecting portion between the C-arm and a C-arm support device in a direction (to be referred to as the second direction hereinafter) perpendicular to the first direction. Note that the C-arm support portion can also support the C-arm so as to make the C-arm movable in the lateral direction (to be referred to as the X direction hereinafter) and longitudinal direction (to be referred to as the Y direction hereinafter) of the tabletop 11 (to be described later).

The support mechanism driving unit 9 drives the support mechanism 7 under the control of the movement control unit 15 (to be described later). More specifically, the support mechanism driving unit 9 slides the C-arm in the first direction (LAO or RAO) by supplying a driving signal corresponding to a control signal from the movement control unit 15 to the C-arm support portion. The support mechanism driving unit 9 rotates the C-arm in the second direction (CRA or CAU) by supplying a driving signal corresponding to a control signal from the movement control unit 15 to the C-arm support portion. The support mechanism driving unit 9 drives the support mechanism 7 under the control of the movement control unit 15 to obtain the SID input from the operator via the input unit 25. The object P is placed on the tabletop 11 between the X-ray generation unit 3 and the X-ray detection unit 5 at the time of X-ray fluoroscopy or X-ray imaging.

The tabletop driving unit 13 drives the tabletop 11 under the control of the movement control unit 15 (to be described later). More specifically, the tabletop driving unit 13 slides the tabletop 11 in the lateral direction or longitudinal direction of the tabletop 11 based on a control signal from the movement control unit 15. In addition, the tabletop driving unit 13 moves the tabletop 11 up and down in the vertical direction. The tabletop driving unit 13 drives the tabletop 11 based on the visual field size and the SID which are input via the input unit 25 under the control of the movement control unit 15.

The movement control unit 15 controls the support mechanism driving unit 9 to locate the center of the FPD at an imaging position and a fluoroscopy position by driving the support mechanism 7. More specifically, the movement control unit 15 outputs, to the support mechanism driving unit 9, a control signal for locating the center of the FPD at an imaging position and a fluoroscopy position.

The thickness decision unit 16 decides the thickness of the object (to be referred to as the object thickness hereinafter) based on a condition concerning the generation of X-rays by the X-ray generation unit 3 (to be referred to as an X-ray condition hereinafter), the dose of X-rays entering the X-ray detection unit 5 (to be referred to as a X-ray detection dose hereinafter), visual field size, SID, and additional filter thickness (including additional filter type). An X-ray condition is, for example, the product (power: kW) of the tube voltage (kV) applied to the X-ray tube and the tube current (mA) supplied to the X-ray tube. A X-ray detection dose is, for example, the dose of X-rays necessary for the generation of an image from an output from the FPD, and is associated with image quality. More specifically, the thickness decision unit 16 decides an object thickness by executing a predetermined calculation using, as input values, the X-ray condition, X-ray detection dose, visual field size, SID, and additional filter thickness (including additional filter type). The thickness decision unit 16 outputs the decided object thickness to the filter specifying unit 17 (to be described later).

The filter specifying unit 17 specifies at least one of the plurality of additional filters in the X-ray beam limiting unit 4 based on an object thickness and an SID. More specifically, the filter specifying unit 17 reads out a correspondence table stored in the storage unit 21 (to be described later). A correspondence table is a correspondence table of additional filters corresponding to object thicknesses and SIDs. The filter specifying unit 17 specifies an additional filter to be placed in front of the X-ray irradiation window from a plurality of additional filters based on the object thickness, SID, and readout correspondence table. If, for example, the object thickness is small and the SID is short, the filter specifying unit 17 specifies a thick additional filter from the plurality of additional filters. If, for example, the object thickness is large and the SID is long, the filter specifying unit 17 specifies a thin additional filter from the plurality of additional filters. The filter specifying unit 17 outputs information concerning the specified additional filter (e.g., an identifier based on the thickness of the additional filter: to be referred to as additional filter specifying information hereinafter) to the X-ray beam limiting control unit 18 (to be described later).

Note that a correspondence table is a correspondence table of the thicknesses of additional filters corresponding to object thicknesses and SIDs. At this time, the filter specifying unit 17 decides the thickness of an additional filter based on the object thickness, SID, and readout correspondence table. The filter specifying unit 17 specifies an additional filter having the decided thickness from the plurality of additional filters.

Figure 2:
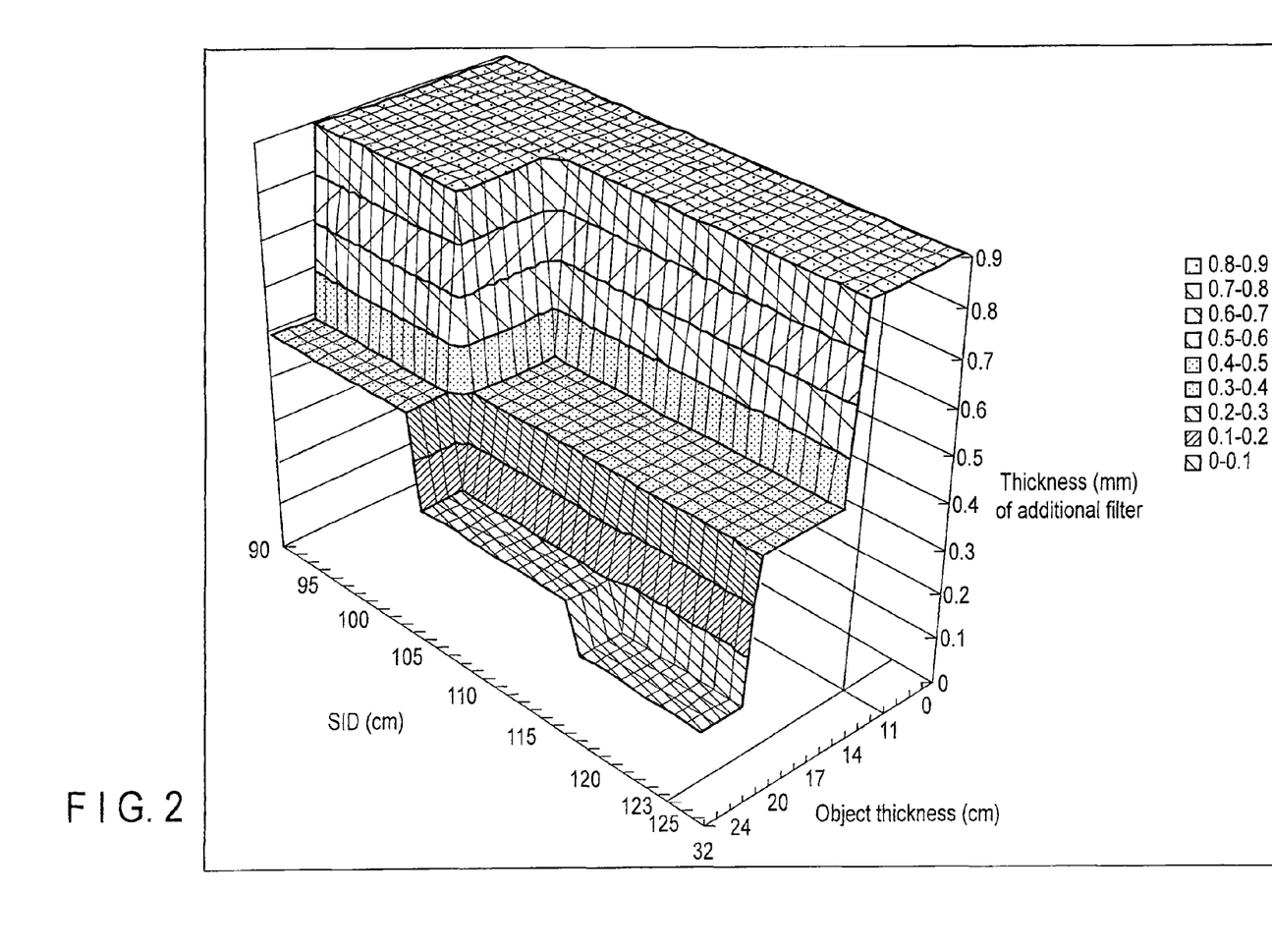
FIG. 2 is a view showing an example of a correspondence table of the thicknesses of additional filters corresponding to object thicknesses and SIDs according to the first embodiment.

FIG. 2 is a view showing an example of how a correspondence table is visualized. The correspondence table shown in FIG. 2 is a correspondence table of the thicknesses of additional filters corresponding to object thicknesses and SIDs. If, for example, the object thickness is 11 cm and the SID is 123 cm, the filter specifying unit 17 decides that the thickness of the additional filter to be used is 0.9 mm. The filter specifying unit 17 then specifies an additional filter having a thickness of 0.9 mm from the plurality of additional filters. Note that the filter specifying unit 17 may specify a combination of two or more additional filters whose sum of thicknesses is 0.9 mm from the plurality of additional filters.

The filter specifying unit 17 may also read out the first and second thresholds from the storage unit 21 before the specification of an additional filter. If the object thickness is equal to or less than the first threshold, the filter specifying unit 17 specifies an additional filter to be placed in front of the X-ray irradiation window regardless of the SID. First of all, the filter specifying unit 17 compares the object thickness with a predetermined threshold. If the object thickness is equal to or more than the predetermined threshold, the filter specifying unit 17 specifies an additional filter corresponding to the object thickness from the plurality of additional filters. If the object thickness exceeds the second threshold, the filter specifying unit 17 specifies an additional filter to be placed in front of the X-ray irradiation window from the plurality of additional filters based on the object thickness, SID, and readout correspondence table.

The X-ray beam limiting control unit 18 controls the X-ray beam limiting unit 4 to place the additional filter specified by the filter specifying unit 17 in front of the X-ray irradiation window. More specifically, the X-ray beam limiting control unit 18 controls the X-ray beam limiting unit 4 to place the additional filter corresponding to the additional filter specifying information output from the filter specifying unit 17 in front of the X-ray irradiation window.

The image generation unit 19 generates a captured image based on the digital data preprocessed after X-ray imaging at an imaging position. The image generation unit 19 generates a fluoroscopic image based on the digital data preprocessed after X-ray fluoroscopy at a fluoroscopy position.

The storage unit 21 stores the various images generated by the image generation unit 19, control programs for the X-ray diagnostic apparatus 1, the diagnostic protocol, instructions sent by the operator from the input unit 25 (to be described later), imaging conditions, various data groups such as fluoroscopy conditions, visual field sizes, SIDs, X-ray detection doses, and the like. The storage unit 21 stores an object thickness calculation program for the execution of predetermined calculations by using an X-ray condition, X-ray detection dose, visual field size, and SID as input values. The storage unit 21 stores a correspondence table of additional filters corresponding to object thicknesses and SIDs. In addition, the storage unit 21 may store the first and second thresholds. Note that the storage unit 21 may store a correspondence table of the thicknesses of additional filters corresponding to object thicknesses and SIDs.

The display unit 23 displays the captured images and fluoroscopic images generated by the image generation unit 19. The display unit 23 displays an input window for inputting an X-ray condition, X-ray detection dose, entrance X-ray dose rate (upper limit value) on the object, visual field size, SID, and the like. Note that the display unit 23 can display a window for inputting an object thickness.

The input unit 25 inputs the imaging conditions for X-ray imaging, fluoroscopy conditions for X-ray fluoroscopy, visual field size, SID, and the like which are desired by the operator. More specifically, the input unit 25 inputs various instructions, commands, information, selections, and settings from the operator to the X-ray diagnostic apparatus 1. The input unit 25 includes a trackball, switch buttons, mouse, and keyboard (none of which are shown) for setting a region of interest and the like. The input unit 25 detects the coordinates of a cursor displayed on the display screen, and outputs the detected coordinates to the system control unit 27 (to be described later). Note that the input device 25 may be a touch panel provided to cover the display screen. In this case, the input unit 25 detects a touched and designated coordinates by a coordinate reading principle such as an electromagnetic induction scheme, magnetostriction scheme, or a pressure-sensitive scheme, and outputs the detected coordinates to the system control unit 27. Note that the input unit 25 can input an object thickness.

The system control unit 27 includes a CPU (Central Processing Unit) and a memory (neither of which is shown). The system control unit 27 controls the X-ray generation unit 3, the X-ray beam limiting control unit 18, the movement control unit 15, and the like to execute X-ray imaging and fluoroscopy in accordance with the instructions, imaging conditions, fluoroscopy conditions, and the like input by the operator via the input unit 25.

(Additional Filter Specifying Function)

The additional filter specifying function is a function of specifying an additional filter to be placed in front of the X-ray irradiation window from a plurality of additional filters based on an object thickness, SID, and readout correspondence table. The processing concerning the additional filter specifying function (to be referred to as additional filter specifying processing hereinafter) will be described below. Note that additional filter specifying function may be executed by using a correspondence table corresponding to the purpose of an examination.

Figure 3:
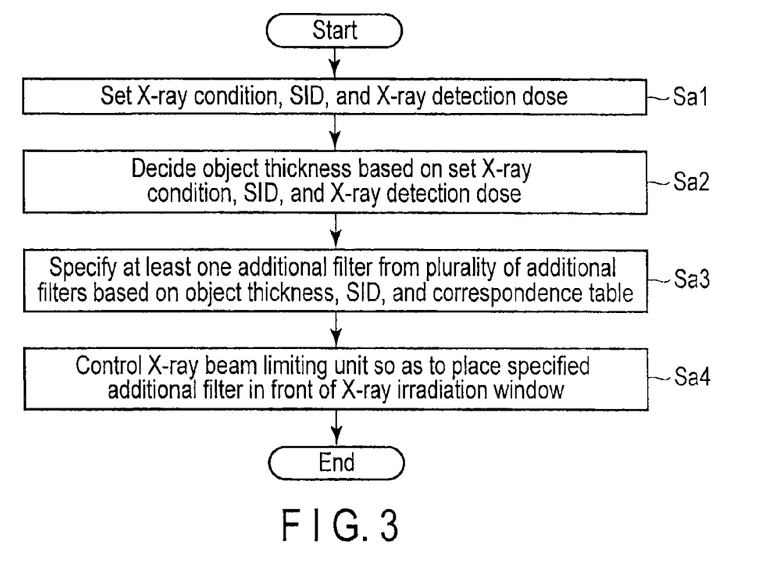
FIG. 3 is a flowchart showing an example of a procedure for deciding an object thickness based on an X-ray condition, SID, X-ray detection dose, and additional filter thickness (including additional filter type) and specifying one additional filter from a plurality of additional filters based on the object thickness and the SID according to the first embodiment.

FIG. 3 is a flowchart showing an example of a procedure for deciding an object thickness based on an X-ray condition, SID, X-ray detection dose, and additional filter thickness (including an additional filter type) and specifying one additional filter from a plurality of additional filters based on the object thickness and the SID according to the first embodiment.

Before X-ray imaging and X-ray fluoroscopy using the X-ray diagnostic apparatus 1, the operator sets an X-ray condition, SID, X-ray detection dose, entrance dose rate (upper limit value) on the object, visual field size, and the like (step Sa1). Note that the operator may input an X-ray condition, SID, X-ray detection dose, entrance dose rate (upper limit value) on the object, visual field size, and the like via, for example, the input unit 25.

The apparatus decides an object thickness by executing a predetermined calculation using the set X-ray condition, SID, X-ray detection dose, visual field size, and additional filter thickness (including additional filter type) as input values (step Sa2). The apparatus then reads out a correspondence table from the storage unit 21. The apparatus specifies at least one additional filter from a plurality of additional filters using the decided object thickness, the decided SID, and the readout correspondence table (step Sa3). The X-ray beam limiting unit 4 is controlled to place the specified additional filter in front of the X-ray irradiation window (step Sa4).

(First Modification)

The first modification differs from the first embodiment in that it stores a plurality of correspondence tables corresponding to X-ray conditions such as a tube voltage and a tube current (or the maximum power of the X-ray tube), and specifies an additional filter to be placed in front of the X-ray irradiation window from the plurality of additional filters based on a correspondence table corresponding to the set X-ray condition, an object thickness, and an SID.

The storage unit 21 stores, for example, a plurality of correspondence tables corresponding to X-ray conditions such as the product of a tube voltage and a tube current (or the maximum power of the X-ray tube). The storage unit 21 stores a plurality of thresholds respectively corresponding to a plurality of correspondence tables.

The filter specifying unit 17 reads out a correspondence table corresponding to set X-ray conditions (e.g., power corresponding to the product of a tube voltage and a tube current) from the storage unit 21. The filter specifying unit 17 specifies an additional filter to be placed in front of the X-ray irradiation window from the plurality of additional filters based on the object thickness, SID, and readout correspondence table. The filter specifying unit 17 outputs additional filter specifying information to the X-ray beam limiting control unit 18.

The filter specifying unit 17 may read out a threshold corresponding to the readout correspondence table from the storage unit 21 before the specification of the additional filter, and perform the following processing. If the object thickness is equal to or less than the first threshold, the filter specifying unit 17 specifies an additional filter placed in front of the X-ray irradiation window regardless of the SID. First of all, the filter specifying unit 17 compares the object thickness with a predetermined threshold. If the object thickness is equal to or less than the first threshold, the filter specifying unit 17 specifies an additional filter corresponding to the object thickness from the plurality of additional filters. Note that if the object thickness exceeds the second threshold, the filter specifying unit 17 specifies an additional filter to be placed in front of the X-ray irradiation window from the plurality of additional filters based on the object thickness, SID, and readout correspondence table.

(Additional Filter Specifying Function)

The additional filter specifying function according to the first modification is a function of reading out a correspondence table corresponding to an X-ray condition from the storage unit 21, and specifying one additional filter from the plurality of additional filters based on the object thickness, SID, and readout correspondence table. Processing concerning the additional filter specifying function according to the first modification will be described later.

Figure 4:
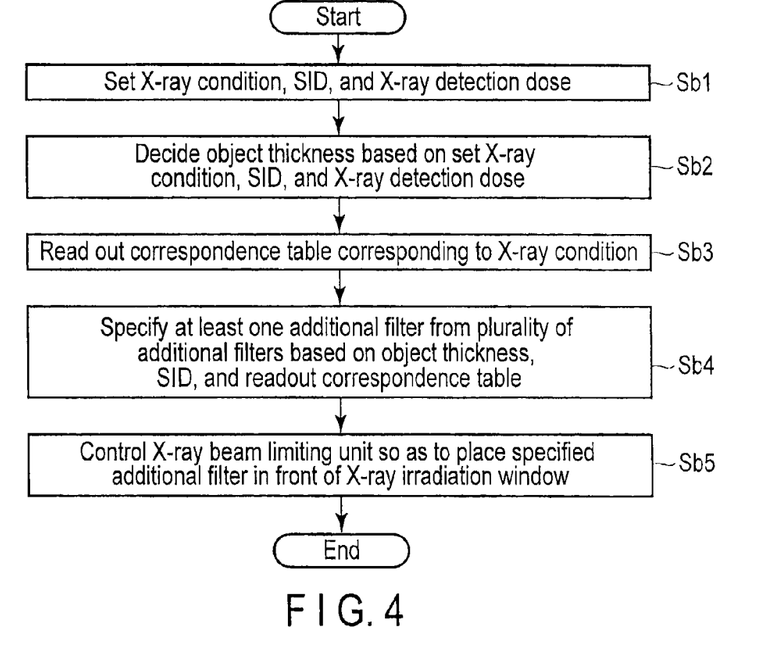
FIG. 4 is a flowchart showing an example of a procedure for reading out a correspondence table corresponding to an X-ray condition (the maximum power of an X-ray tube) and specifying one additional filter from a plurality of additional filters based on the object thickness, SID, and readout correspondence table according to the first modification of the first embodiment.

FIG. 4 is a flowchart showing an example of a procedure for reading out a correspondence table corresponding to an X-ray condition (the maximum power of the X-ray tube) and specifying one additional filter from a plurality of additional filters based on an object thickness, SID, and correspondence table according to the first modification of the first embodiment.

Before X-ray imaging and X-ray fluoroscopy by the X-ray diagnostic apparatus 1, the operator sets an X-ray condition, SID, X-ray detection dose, entrance dose rate (upper limit value) on the object, visual field size, and the like (step Sb1). Note that the operator may input an X-ray condition, SID, X-ray detection dose, entrance dose rate (upper limit value) on the object, visual field size, and the like via, for example, the input unit 25.

The apparatus decides an object thickness by executing a predetermined calculation using the set X-ray condition, SID, X-ray detection dose, visual field size, and additional filter thickness (including additional filter type) as input values (step Sb2). The apparatus then reads out a correspondence table from the storage unit 21 (step Sb3).

FIG. 5 is a view showing an example of a correspondence table of additional filters corresponding to X-ray conditions, entrance dose rates (upper limit values) on objects, SIDs, and object thicknesses. In FIG. 5, (a) indicates an example of a correspondence table corresponding to a maximum power (kW) of 3 kW as an X-ray condition in the X-ray fluoroscopy method. In FIG. 5, (b) indicates an example of a correspondence table corresponding to a maximum power (kW) of 2.2 kW as an X-ray condition in the pulse X-ray fluoroscopy method. The first to seventh filters in FIG. 5 are additional filters having different thicknesses. Of the first to seventh additional filters, the first additional filter is the thickest additional filter, and the seventh additional filter is the thinnest additional filter.

At least one additional filter is specified from the plurality of additional filters by using the decided object thickness, SID, and readout correspondence table (step Sb4). The X-ray beam limiting unit 4 is controlled to place the specified additional filter in front of the X-ray irradiation window (step Sb5).

According to the above arrangement, the following effects can be obtained.

The X-ray diagnostic apparatus 1 according to this embodiment can decide an object thickness based on an X-ray condition, X-ray detection dose, visual field size, SID, and additional filter thickness (including an additional filter type), and more accurately specify additional filters suitable for X-ray imaging and X-ray fluoroscopy based on the decided object thickness, SID, and correspondence table. This makes it possible to maximize the utilization of the capacity to generate X-rays in the X-ray diagnostic apparatus 1. In addition, it is possible to minimize the exposure dose on the object. Furthermore, the X-ray diagnostic apparatus 1 can use a correspondence table used for specifying an additional filter in accordance with an X-ray condition. This allows to use an optimal additional filter in accordance with an X-ray condition (e.g., the capacity of the X-ray tube). In addition, it is possible to use an optimal additional filter in accordance with a rise in the accumulated anode heat of the X-ray tube and a deterioration in quality over time even when the capacity of the X-ray tube has deteriorated.

As described above, the X-ray diagnostic apparatus 1 according to this embodiment can always use an additional filter giving priority to a reduction in exposure dose on an object with a small object thickness. In addition, even for an object with a large object thickness, it is possible to effectively use the capacity of the X-ray tube, if the SID is short, and hence to reduce exposure dose on an object with a large object thickness.

(Second Embodiment)

The same reference numerals as in the first embodiment denote the same constituent elements in the second embodiment to avoid a repetitive description. Therefore, a detailed description of them will be omitted, and only different constituent elements will be described below.

Figure 6:
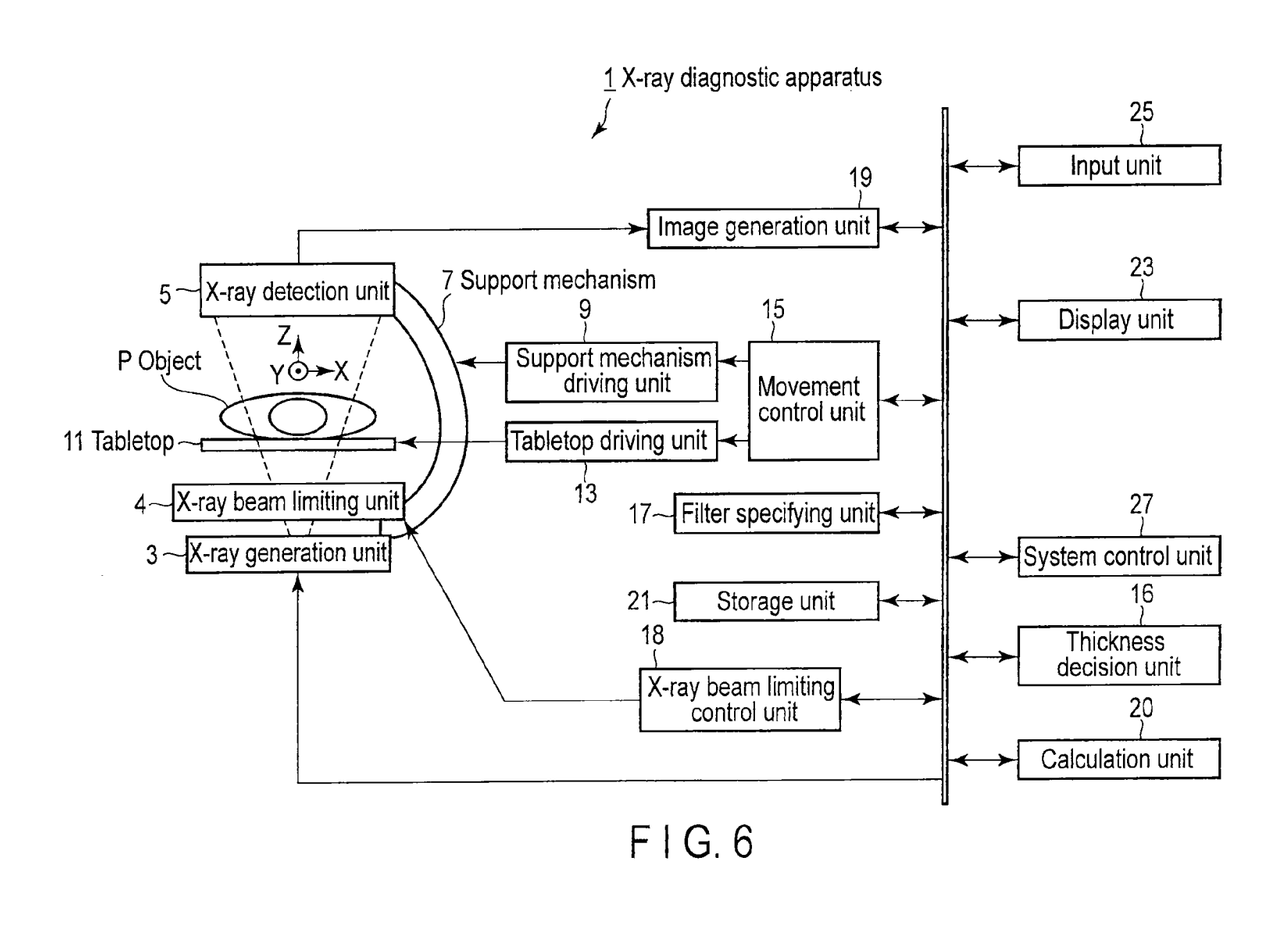
FIG. 6 is a view showing an example of the arrangement of an X-ray diagnostic apparatus according to the second embodiment.

FIG. 6 is a view showing the arrangement of an X-ray diagnostic apparatus according to the second embodiment.

A storage unit 21 stores the data of the first phantom having the same thickness as an object thickness. The first phantom data is, for example, data having the same X-ray attenuation coefficient as that of water. The storage unit 21 stores the data of the second phantom having a predetermined thickness smaller than the object thickness. The second phantom data is data having the same X-ray attenuation coefficient as that of a contrast medium. The predetermined thickness is, for example, the diameter of a blood vessel. The storage unit 21 stores a correspondence table of additional filters corresponding to object thicknesses, SIDs, and the contrast values calculated by a calculation unit 20 (to be described later). More specifically, a correspondence table in the second embodiment is, for example, a correspondence table having a contrast value added to the items of the correspondence table shown in FIG. 5 in the first embodiment. An additional filter in a correspondence table concerning the second embodiment is an additional filter which improves a contrast value. Note that the storage unit 21 may store the X-ray attenuation coefficient of water, the X-ray attenuation coefficient of a contrast medium, and a predetermined thickness instead of the first and second phantom data.

The calculation unit 20 calculates, by using an X-ray condition and the first phantom data, the first signal value expected to be output from an X-ray detection unit 5 when the X-rays generated under the X-ray condition are transmitted through the first phantom. The calculation unit 20 calculates, by using an X-ray condition and the second phantom data, the second signal value expected to be output from the X-ray detection unit 5 when the X-rays generated under the X-ray condition are transmitted through the second phantom. The calculation unit 20 calculates the ratio of the second signal value to the first signal value (to be referred to as a contrast value hereinafter). Note that the calculation unit 20 may calculate, as a contrast value, the ratio of the first signal value to the second signal value. Note that if the storage unit 21 does not store the first and second phantom data, the calculation unit 20 can generate (calculate) the first phantom data based on the X-ray attenuation coefficient of water and object thickness stored in the storage unit 21 before calculating the first and second signal values. The calculation unit 20 then generates (calculates) the first phantom based on the X-ray attenuation coefficient of water and object thickness stored in the storage unit 21. Finally, the calculation unit 20 generates (calculates) the second phantom data based on the X-ray attenuation coefficient of a contrast medium and predetermined thickness stored in the storage unit 21.

A filter specifying unit 17 specifies at least one of a plurality of additional filters in an X-ray beam limiting unit 4 based on an object thickness, SID, and contrast value. More specifically, the filter specifying unit 17 reads out a correspondence table stored in the storage unit 21. A correspondence table is a correspondence table of additional filters corresponding to object thicknesses, SIDs, and contrast values. The filter specifying unit 17 specifies an additional filter to be placed in front of the X-ray irradiation window from a plurality of additional filters based on the object thickness, SID, contrast value, and readout correspondence table. Assume that the object thickness is small, the SID is short, and the contrast value is large. In this case, the filter specifying unit 17 specifies a thick additional filter. Assume that the object thickness is large, the SID is long, and the contrast value is small. In this case, the filter specifying unit 17 specifies a thin additional filter. The filter specifying unit 17 outputs information concerning the specified additional filter (e.g., an identifier based on the thickness of the additional filter: to be referred to as additional filter specifying information hereinafter) to an X-ray beam limiting control unit 18 (to be described later).

(Additional Filter Specifying Function)

This embodiment differs from the first embodiment in that it calculates a contrast value based on an object thickness, X-ray condition, and first and second phantom data, and specifies one additional filter from a plurality of additional filters based on the calculated contrast value, object thickness, and SID. Processing concerning the additional filter specifying function in the second embodiment will be described below.

Figure 7:
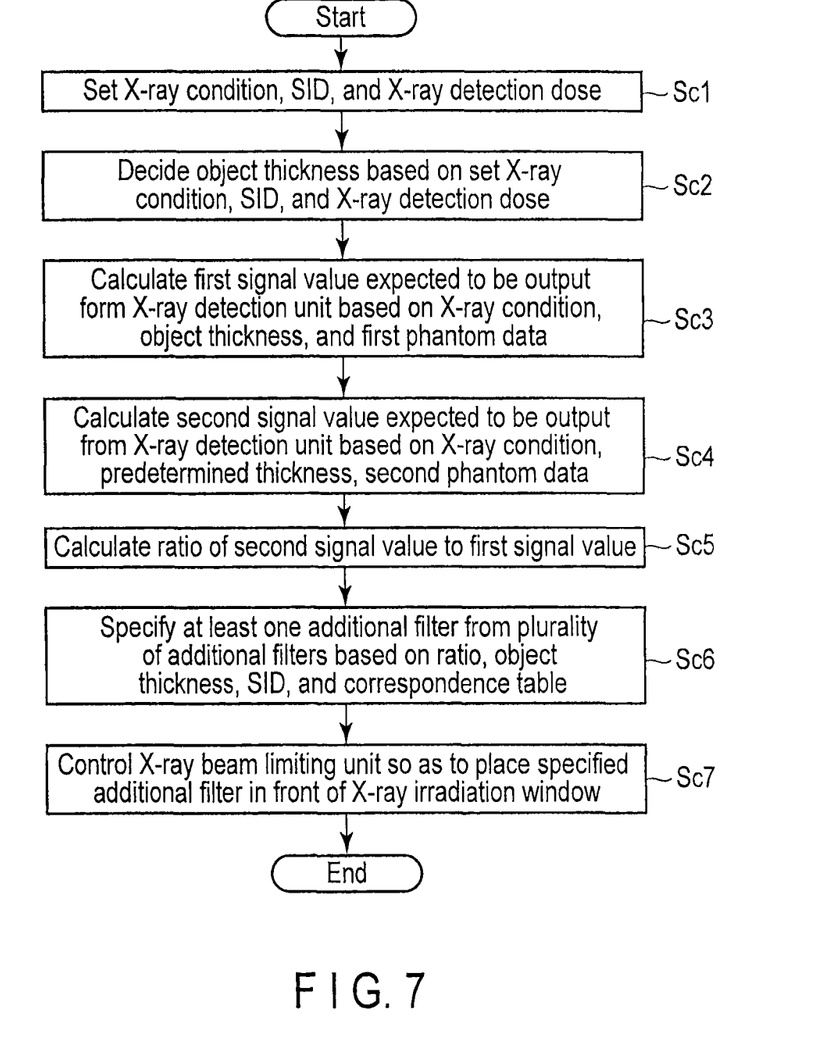
FIG. 7 is a flowchart showing an example of a procedure for calculating a contrast value based on an object thickness, X-ray condition, and first and second phantom data, and specifying one additional filter from a plurality of additional filters based on the contrast value, object thickness, and SID according to the second embodiment.

FIG. 7 is a flowchart showing an example of a procedure for calculating a contrast value based on an object thickness, X-ray condition, and first and second phantom data, and specifying one additional filter from a plurality of additional filters based on the calculated contrast value, object thickness, and SID according to the second embodiment.

Before X-ray imaging and X-ray fluoroscopy using the X-ray diagnostic apparatus 1, the operator sets an X-ray condition, SID, X-ray detection dose, visual field size, and the like (step Sol). Note that the operator may input an X-ray condition, SID, X-ray detection dose, visual field size, and the like via, for example, an input unit 25.

The apparatus decides an object thickness by executing a predetermined calculation using the set X-ray condition, SID, X-ray detection dose, visual field size, and additional filter thickness (including additional filter type) as input values (step Sc2). The apparatus reads out the first phantom data. The apparatus calculates the first signal value expected to be output from the X-ray detection unit 5 based on the X-ray condition, object thickness, and first phantom data (step Sc3). The apparatus then reads out the second phantom data. The apparatus calculates the second signal value expected to be output from the X-ray detection unit 5 based on the X-ray condition, the predetermined thickness, and second phantom data (step Sc4). The apparatus calculates a contrast value as the ratio of the second signal value to the first signal value (step Sc5).

The apparatus then reads out a correspondence table from the storage unit 21. The apparatus specifies at least one additional filter from a plurality of additional filters using the contrast value, SID, and readout correspondence table (step Sc6). The X-ray beam limiting unit 4 is controlled to place the specified additional filter in front of the X-ray irradiation window (step Sc7).

(Second Modification)

The second modification differs from the second embodiment in that it specifies one additional filter from a plurality of additional filters based on the examination region, contrast value, object thickness, and SID which are input via the input unit 25.

The input unit 25 inputs the examination region of the object. Note that the input unit 25 may input an examination protocol instead of an examination region. It is also possible to transfer an examination region or an examination protocol from a hospital information system or a radiology information system connected via an interface (not shown).

The storage unit 21 stores a correspondence table of additional filters corresponding to examination regions, object thicknesses, SIDs, and contrast values. More specifically, a correspondence table in the second modification is, for example, a correspondence table having a contrast value and an examination region added to the items of the correspondence table shown in FIG. 5 in the first embodiment. An additional filter in a correspondence table concerning the second modification is an additional filter which is used to improve a contrast value or an additional filter which is used to reduce the exposure dose on an object. Note that the storage unit 21 can store a plurality of correspondence tables in accordance with purposes such as reducing the exposure dose on an object and improving a contrast value. Alternatively, the storage unit 21 may store a plurality of correspondence tables respectively corresponding to a plurality of examination regions. Note that the storage unit 21 may store a correspondence table assigning priority levels to exposure doses on an object and the qualities of images displayed on the display unit 23.

The filter specifying unit 17 specifies at least one of a plurality of additional filters in the X-ray beam limiting unit 4 based on an examination region, object thickness, SID, and contrast value. More specifically, the filter specifying unit 17 reads out a correspondence table stored in the storage unit 21. A correspondence table is a correspondence table of additional filters corresponding to examination regions, object thicknesses, SIDs, and contrast values. Note that the filter specifying unit 17 may read out a correspondence table based on the input of priority levels assigned to exposure doses on the object and image qualities corresponding to examination contents. The filter specifying unit 17 specifies an additional filter to be placed in front of the X-ray irradiation window from a plurality of additional filters based on the examination region, object thickness, SID, contrast value, and readout correspondence table. Assume that the object thickness is small, the SID is long, the contrast value is large, and the examination region is the head portion. In this case, the filter specifying unit 17 specifies a thick additional filter. Assume that that the object thickness is large, the SID is short, the contrast value is small, and the examination region is the abdominal portion. In this case, the filter specifying unit 17 specifies a thin additional filter. The filter specifying unit 17 outputs information concerning the specified additional filter (e.g., an identifier based on the thickness of the additional filter: to be referred to as additional filter specifying information hereinafter) to the X-ray beam limiting control unit 18 (to be described later).

(Additional Filter Specifying Function)

This additional filter specifying function differs from that in the second embodiment in that an examination region is set, and at least one additional filter of a plurality of additional filters is specified by using the set examination region, a contrast value, an object thickness, an SID, and a readout correspondence table.

Figure 8:
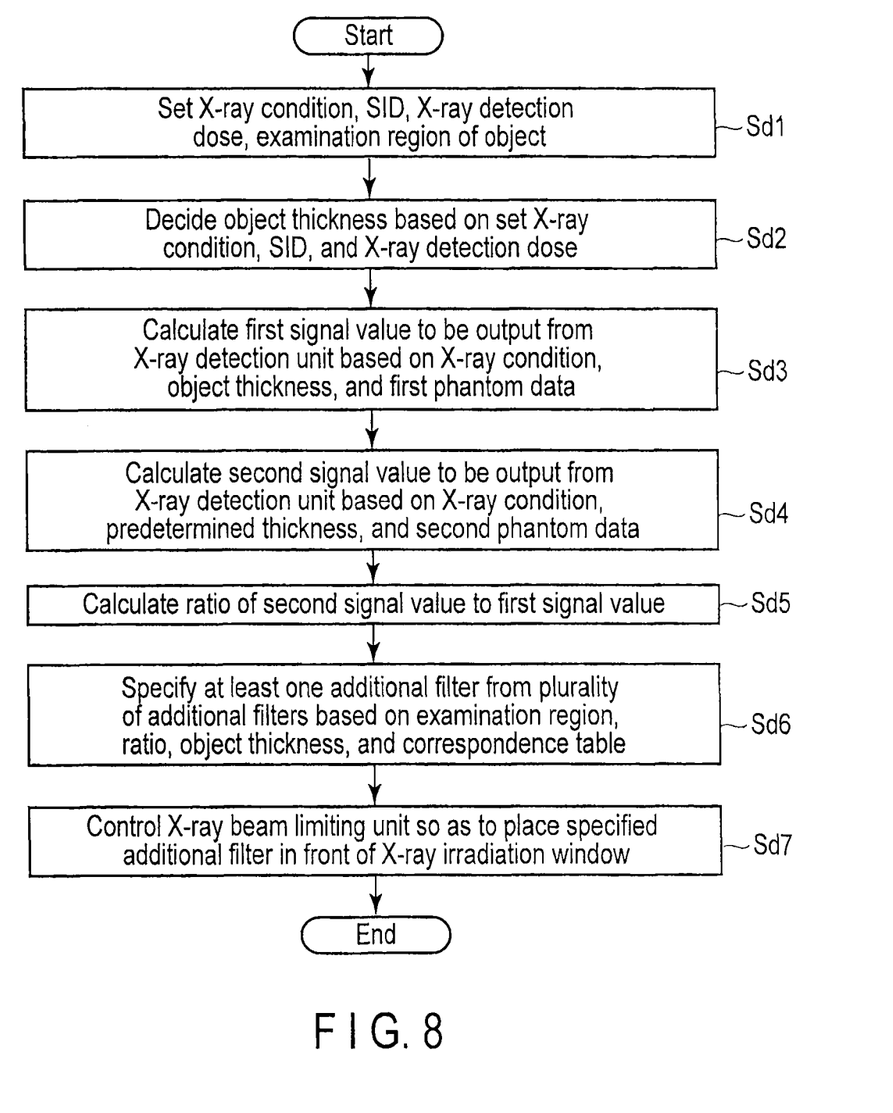
FIG. 8 is a flowchart showing an example of a procedure for specifying one additional filter from a plurality of additional filters based on a contrast value, object thickness, SID, and examination region of an object according to the second modification of the second embodiment.

FIG. 8 is a flowchart showing an example of a procedure for specifying one additional filter from a plurality of additional filters based on a contrast value, object thickness, SID, and examination region of an object.

Before X-ray imaging and X-ray fluoroscopy using the X-ray diagnostic apparatus 1, the operator sets an examination region of an object, X-ray condition, SID, X-ray detection dose, visual field size, and the like (step Sd1). Note that the operator may input an examination region of an object, X-ray condition, SID, X-ray detection dose, visual field size, and the like via, for example, the input unit 25.

The apparatus decides an object thickness by executing a predetermined calculation using the set X-ray condition, SID, X-ray detection dose, visual field size, and additional filter thickness (including additional filter type) as input values (step Sd2). The apparatus reads out the first phantom data. The apparatus calculates the first signal value expected to be output from the X-ray detection unit 5 based on the X-ray condition, object thickness, and first phantom data (step Sd3). The apparatus then reads out the second phantom data. The apparatus calculates the second signal value expected to be output from the X-ray detection unit 5 based on the X-ray condition, object thickness, and second phantom data (step Sd4). The apparatus calculates a contrast value as the ratio of the second signal value to the first signal value (step Sd5).

The apparatus then reads out a correspondence table from the storage unit 21. The apparatus specifies at least one additional filter from a plurality of additional filters using the examination region, contrast value, SID, and readout correspondence table (step Sd6). The X-ray beam limiting unit 4 is controlled to place the specified additional filter in front of the X-ray irradiation window (step Sd7).

According to the above arrangement, the following effects can be obtained.

The X-ray diagnostic apparatus 1 according to this embodiment can decide an object thickness based on an X-ray condition, X-ray detection dose, visual field size, SID, additional filter thickness (including additional filter type), and calculate a contrast value based on the decided object thickness and the X-ray condition. The X-ray diagnostic apparatus 1 can specify an additional filter suitable for X-ray imaging and X-ray fluoroscopy more precisely based on a contrast value, object thickness, SID, and correspondence table. This makes it possible for the X-ray diagnostic apparatus 1 to make the most use of the capacity to generate X-rays. In addition, it is possible to minimize the exposure dose on an object. Furthermore, the X-ray diagnostic apparatus 1 specifies an additional filter in consideration of a contrast value, and hence can specify an additional filter without degrading the quality of an image displayed on the display unit 23.

In addition, the X-ray diagnostic apparatus 1 can read out a correspondence table used to specify an additional filter in accordance with an examination region or an examination protocol. This makes it possible to specify an additional filter in accordance with how priority is assigned to an exposure dose on an object and image quality.

As has been described above, the X-ray diagnostic apparatus 1 according to this embodiment can use an additional filter optimal for an X-ray condition, object thickness, and the like, and provide an optimal image corresponding to the examination contents of the object. In addition, it is possible to, for example, shorten the diagnosis time, perform accurate diagnosis, and reduce the exposure dose.

Furthermore, each function according to the embodiment can be implemented by installing programs for executing the processing in a computer such as a workstation and expanding them in the memory. In this case, the programs which can cause the computer to execute the corresponding techniques can be distributed by being stored in storage media such as magnetic disks (floppy® disks, hard disks, and the like), optical disks (CD-ROMs, DVDs, and the like), and semiconductor memories.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray diagnostic apparatus comprising:
an X-ray generation unit configured to generate X-rays;
an X-ray detection unit configured to detect the X-rays generated by the X-ray generation unit and transmitted through an object placed on a tabletop;
an X-ray beam limiting unit including a plurality of filters configured to harden radiation quality of the generated X-rays; and
an X-ray beam limiting control unit configured to control the X-ray beam limiting unit to place a filter of the plurality of filters between the X-ray generation unit and the object, said filter of the plurality of filters being specified based on a thickness of the object and a distance between the X-ray generation unit and the X-ray detection unit.

2. The apparatus of claim 1, further comprising a filter specifying unit configured to specify at least one filter of the plurality of filters based on the thickness of the object and the distance between the X-ray generation unit and the X-ray detection unit,
wherein the X-ray beam limiting control unit is configured to control the X-ray beam limiting unit to place the specified filter between the X-ray generation unit and the object.

3. An X-ray diagnostic apparatus comprising:
an X-ray generation unit configured to generate X-rays;
an X-ray detection unit configured to detect the X-rays generated by the X-ray generation unit and transmitted through an object placed on a tabletop;
an X-ray beam limiting unit including a plurality of filters configured to harden radiation quality of the generated X-rays;
a filter specifying unit configured to specify at least one filter of the plurality of filters based on a thickness of the object and a distance between the X-ray generation unit and the X-ray detection unit; and
an X-ray beam limiting control unit configured to control the X-ray beam limiting unit to place the specified filter between the X-ray generation unit and the object.

4. The apparatus of claim 3, further comprising a thickness decision unit configured to decide the thickness of the object based on an X-ray condition for generation of the X-rays, an X-ray dose entering the X-ray detection unit, the distance, and thicknesses of the filters,
wherein the filter specifying unit is configured to specify said at least one filter of the plurality of filters based on the distance and the decided thickness.

5. The apparatus of claim 3, further comprising a storage unit configured to store a correspondence table of the filters in association with the thickness of the object and the distance,
wherein the filter specifying unit specifies said at least one filter of the plurality of filters based on the thickness of the object, the distance, and the correspondence table.

6. The apparatus of claim 3, further comprising a calculation unit configured to
calculate a first signal value using an X-ray condition for generation of the X-rays and data of a first phantom having a thickness same as the thickness of the object, the first signal value representing an output from the X-ray detection unit when X-rays generated under the X-ray condition are transmitted through the first phantom,
calculate a second signal value using the X-ray condition and data of a second phantom concerning a contrast medium and having a predetermined thickness smaller than the thickness of the object, the second signal value representing an output from the X-ray detection unit when X-rays generated under the X-ray condition are transmitted through the second phantom, and
calculate a ratio of the second signal value to the first signal value,
wherein the filter specifying unit is configured to specify said at least one filter of the plurality of filters based on the distance, the thickness of the object, and the ratio.

7. The apparatus of claim 6, further comprising an input unit configured to input an examination region of the object,
wherein the filter specifying unit is configured to specify said at least one filter of the plurality of filters based on the examination region, the distance, the thickness of the object, and the ratio.

8. The apparatus of claim 3, wherein the filter specifying unit is configured to specify said at least one filter of the plurality of filters based on an X-ray condition for generation of the X-rays by the X-ray generation unit, the distance, and the thickness of the object.

9. The apparatus of claim 8, further comprising a storage unit configured to store a correspondence table of thicknesses of the filters in association with the thickness of the object and the distance, the correspondence table corresponding to each of a plurality of X-ray conditions for generation of the X-rays, wherein the filter specifying unit is configured to specify said at least one filter of the plurality of filters based on the correspondence table corresponding to the X-ray condition, the thickness of the object, and the distance.

10. The apparatus of claim 3, further comprising:

a storage unit configured to store a correspondence table of the filters in association with the thickness of the object, the distance, and an upper limit value of a rate of entrance dosage to the object; and an input unit configured to input the distance and the upper limit value, wherein the filter specifying unit is configured to specify said at least one filter of the plurality of filters based on the thickness of the object, the distance, the upper limit value, and the correspondence table.

11. An X-ray beam limiting control method comprising:

specifying at least one filter of a plurality of filters configured to harden radiation quality of X-rays, based on a thickness of an object and a distance between an X-ray generation unit configured to generate the X-rays and an X-ray detection unit configured to detect the X-rays generated by the X-ray generation unit; and placing the specified filter between the X-ray generation unit and the object.

* * * * *